(12) United States Patent
Wiemeyer et al.

(10) Patent No.: US 8,491,650 B2
(45) Date of Patent: Jul. 23, 2013

(54) TRANSCATHETER PROSTHETIC HEART VALVE DELIVERY SYSTEM AND METHOD WITH STRETCHABLE STABILITY TUBE

(75) Inventors: Nathan Wiemeyer, Santa Rosa, CA (US); Robert Murray, III, Santa Rosa, CA (US); Siyan Som, Fulton, CA (US); Susheel Deshmukh, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 265 days.

(21) Appl. No.: 12/756,843

(22) Filed: Apr. 8, 2010

(65) Prior Publication Data

US 2011/0251679 A1    Oct. 13, 2011

(51) Int. Cl.
*A61F 2/24* (2006.01)

(52) U.S. Cl.
USPC .................................... 623/2.11; 623/1.11

(58) Field of Classification Search
USPC ............... 623/1.11, 2.1, 2.11, 2.12; 606/108, 606/191, 194, 198, 200
See application file for complete search history.

(56) References Cited

U.S. PATENT DOCUMENTS

| | | | |
|---|---|---|---|
| 5,683,451 A | 11/1997 | Lenker et al. | |
| 5,824,041 A | 10/1998 | Lenker et al. | |
| 5,906,619 A | 5/1999 | Olson et al. | |
| 2003/0040789 A1* | 2/2003 | Colgan et al. | 623/1.11 |
| 2004/0059292 A1* | 3/2004 | Hisamatsu et al. | 604/103.04 |
| 2004/0087968 A1* | 5/2004 | Core | 606/108 |
| 2005/0080430 A1* | 4/2005 | Wright et al. | 606/108 |
| 2006/0265056 A1 | 11/2006 | Nguyen et al. | |
| 2007/0073391 A1* | 3/2007 | Bourang et al. | 623/2.11 |
| 2007/0088431 A1 | 4/2007 | Bourang et al. | |
| 2007/0239266 A1 | 10/2007 | Birdsall | |
| 2007/0239269 A1 | 10/2007 | Dolan et al. | |
| 2008/0147182 A1* | 6/2008 | Righini et al. | 623/2.11 |
| 2009/0171456 A1* | 7/2009 | Kveen et al. | 623/2.11 |

* cited by examiner

*Primary Examiner* — S. Thomas Hughes
*Assistant Examiner* — Katherine M Shi

(57) ABSTRACT

A device for percutaneously delivering a stented prosthetic heart valve. The device includes an inner shaft, a delivery sheath, stability tube, and a handle. The delivery sheath is slidably disposed over the inner shaft, and includes a capsule compressively containing the prosthesis over the inner shaft. The stability tube is coaxially received over the delivery sheath, and includes a distal region. A circumferential rigidity of the capsule is greater than a circumferential rigidity of the distal region. In transitioning from a delivery state to a deployed state, the capsule is withdrawn from the prosthetic heart valve and at least partially into the distal region to permit the prosthesis to self-deploy. The capsule forces the distal region to stretch and expand in diameter.

25 Claims, 13 Drawing Sheets

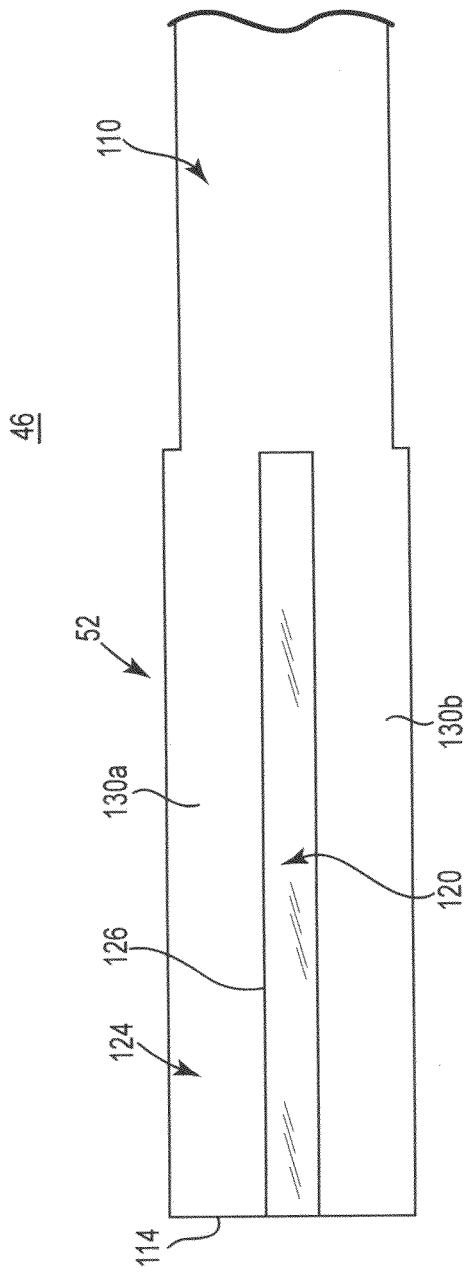
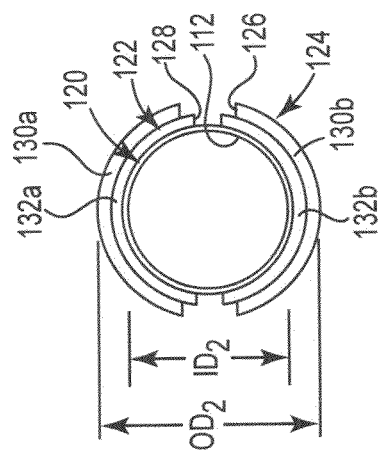

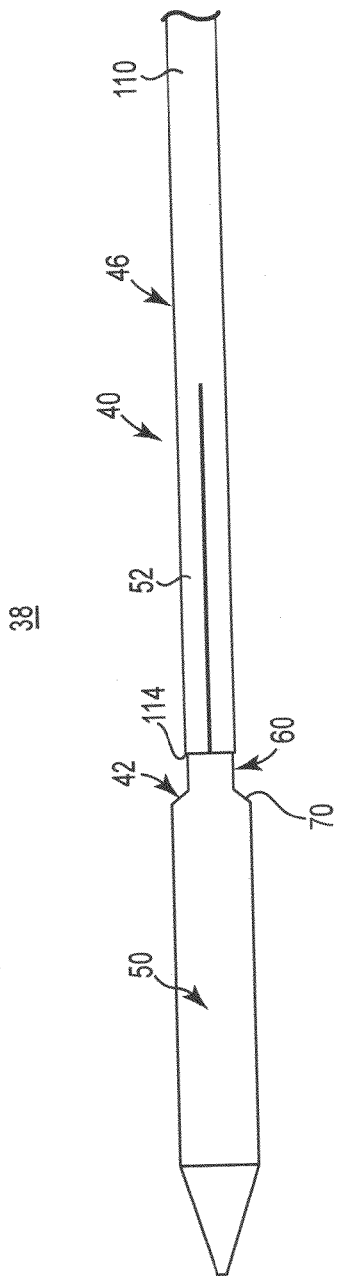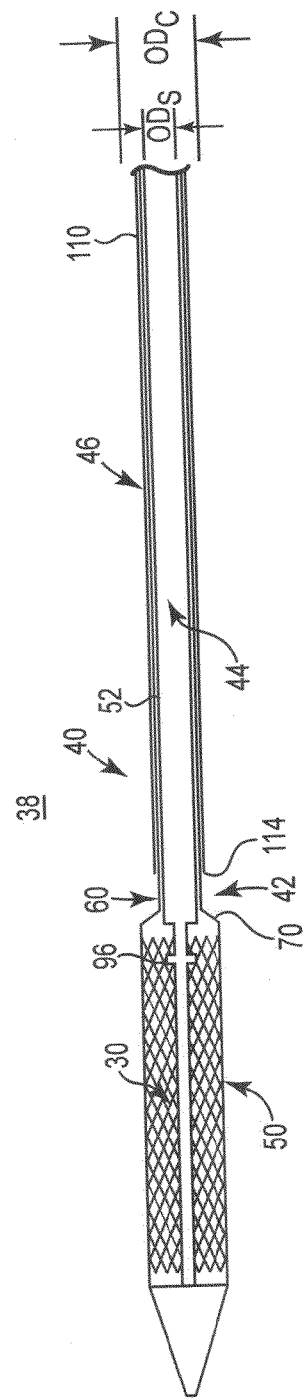

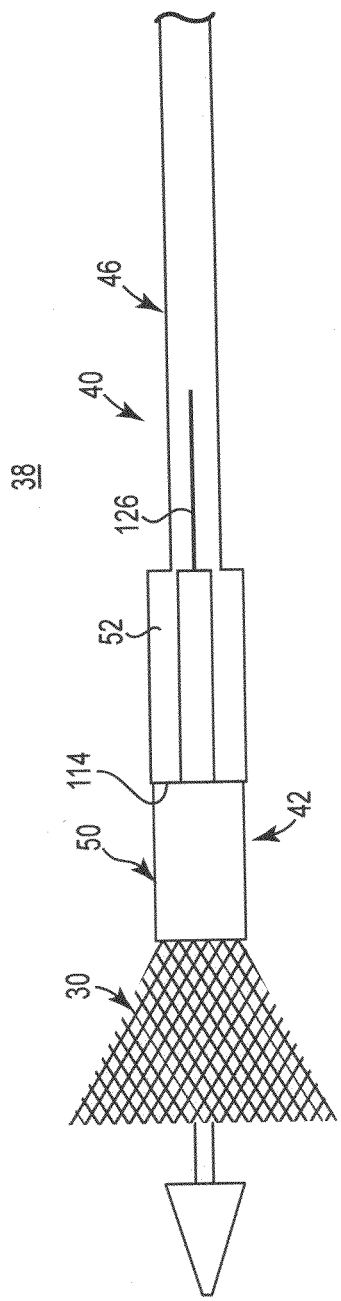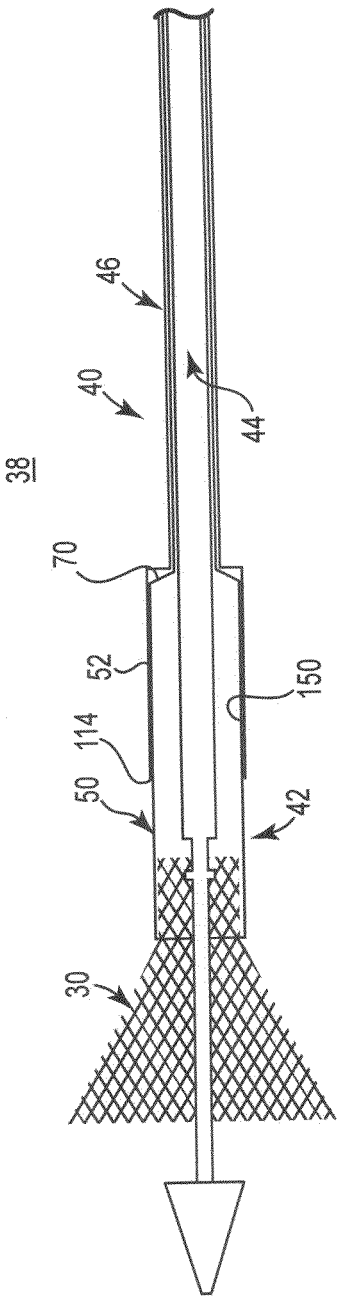
Fig. 8A
Fig. 8B

TRANSCATHETER PROSTHETIC HEART VALVE DELIVERY SYSTEM AND METHOD WITH STRETCHABLE STABILITY TUBE

BACKGROUND

The present disclosure relates to systems and methods for percutaneous implantation of a prosthetic heart valve. More particularly, it relates to systems and methods for transcatheter implantation of a stented prosthetic heart valve.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter-based delivery device and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular transcatheter prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). Oftentimes, the stent frame of the valved stent is made of a self-expanding material and construction. The corresponding percutaneous delivery/implantation devices generally assume one of two forms. In many instances, the delivery device is constructed such that the valved stent is crimped down to a desired size and held in that compressed arrangement within an outer delivery sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of a catheter until it is as close to the diameter of the catheter as possible. The so-loaded balloon catheter is slidably disposed within an outer delivery sheath. Once delivered to the implantation site, the prosthesis is removed from the delivery sheath and the balloon is inflated to deploy the prosthesis. With either of these types of percutaneous stented prosthetic valve delivery devices, conventional sewing of the prosthesis to the patient's native tissue is typically not necessary.

In addition to the delivery device itself, typical transcatheter heart valve implantation techniques entail the use of a separate introducer device to establish a portal to the patient's vasculature (e.g., femoral artery) and through which the prosthetic heart valve-loaded delivery device is inserted. The introducer device generally includes a relatively short sheath and a valve structure. By inserting the prosthesis-containing delivery sheath through the introducer valve and sheath, a low-friction hemostasis seal is created around the outer surface of the delivery sheath. While highly desirable, friction between the introducer device and the delivery sheath can be problematic, leading to unexpected movement of the prosthesis prior to release from the delivery device.

In particular, with a self-expanding stented prosthetic heart valve, the outer delivery catheter or sheath is retracted from over the prosthesis, thereby permitting the stented valve to self-expand and release from the delivery device. Friction between the introducer device and the delivery sheath has a tendency to resist necessary proximal movement of the delivery sheath. Because the retraction force is initiated at a handle of the delivery device, this resistance is transferred to the handle. As a result, unless the clinician (and/or an assistant) carefully holds both the handle and the introducer device in a fixed position relative to one another throughout the deployment operation, the handle has a tendency to draw forward. This movement, in turn, is transferred onto the delivery device component (e.g., an internal shaft) otherwise coupled to the loaded prosthetic heart valve, potentially moving the internal component (including the loaded prosthetic heart valve) forward or distally within the patient. While unintended, even a slight displacement from the expected deployment location of the prosthesis relative to the native annulus can lead to severe complications as the prosthesis must intimately lodge and seal against the native annulus for the implantation to be successful. If the deployed prosthesis is incorrectly positioned relative to the native annulus, the deployed stented valve may leak or even dislodge from the implantation site.

For example, FIG. 1A illustrates, in simplified form, an introducer device 10 establishing a portal to a patient's vasculature 12, and through which a prosthetic heart valve-loaded delivery shaft 14 (the tip of which is visible in FIG. 1A) has been inserted. As shown, the delivery shaft 14 has been manipulated to locate the loaded prosthetic heart valve 16 (referenced generally) in a desired position relative to an aortic valve 18. An outer delivery sheath 20 contains the prosthesis 16. Thus, in the state of FIG. 1A, the prosthetic heart valve 16 is properly positioned for deployment from the delivery shaft 14 upon proximal retraction of the delivery sheath 20 relative thereto, with a spacing S being established between a distal end of the delivery device's handle 22 and the introducer device 10. As shown in FIG. 1B, an actuator 24 of the handle 22 is moved by the clinician in an attempt to proximally pull or retract the delivery sheath 20 and release the prosthesis 16. Frictional interface between the delivery sheath 20 and the introducer device 10 may resist proximal movement of the delivery sheath 20 (conventionally, the introducer device 10 is held stationary). As a result, the handle 22 is instead pulled forward toward the introducer device 10 (reflected in FIG. 1B by a decrease in the spacing S). In effect, the handle 22 is being advanced over the delivery sheath 20 rather than the delivery sheath 20 being retracted into the handle 22. Forward movement of the handle 22 is, in turn, directed onto the delivery shaft 14, causing the delivery shaft 14 to distally advance (represented by the arrow B in FIG. 1B) and displace the deploying prosthetic heart valve 16 from the desired valve implantation site 18. While it may be possible to provide an additional isolation layer between the introducer device 10 and the delivery sheath 20, distinct constraints render implementation of an additional layer highly problematic. For example, the tortuous nature of the patient's vasculature necessitates that the delivery device have as low a profile as possible, thereby limiting an available size of the additional layer. Conversely, any additional layers must account for and facilitate necessary retraction of the delivery sheath 20 during a deployment operation.

In light of the above, although there have been advances in percutaneous valve replacement techniques and devices, there is a continued desired to provide different delivery systems for delivering cardiac replacement valves, and in particular self-expanding, stented prosthetic heart valves to an implantation site in a minimally invasive and/or percutaneous manner.

SUMMARY

Some aspects in accordance with principles of the present disclosure relate to a delivery device for percutaneously delivering a stented prosthetic heart valve. The prosthetic heart valve is radially self-expandable from a compressed arrangement to a normal, expanded arrangement. With this in mind, the delivery device includes an inner shaft assembly, a delivery sheath assembly, an outer stability tube, and a handle. The inner shaft assembly includes a coupling structure configured to selectively engage the prosthetic heart valve. The delivery sheath assembly is slidably disposed over the inner shaft assembly and includes a distal capsule and a proximal shaft. The capsule is configured to contain the prosthetic heart valve in a compressed arrangement. The stability tube is coaxially received over the shaft, and includes a proximal region and a distal region. In this regard, a circumferential rigidity of the capsule is greater than a circumferential rigidity of the distal region. Finally, the handle includes a housing and an actuator mechanism coupled to the delivery sheath shaft and operable to selectively move the delivery sheath assembly relative to the inner shaft assembly and the stability tube. In a delivery state of the device, the capsule compressively contains the prosthetic heart valve and the distal region of the stability tube is proximal the capsule. An inner diameter of the distal region is less than an outer diameter of the capsule. In a deployed state, the capsule is withdrawn from the prosthetic heart valve and at least partially into the distal region to thereby permit the prosthetic heart valve to self-deploy. In this regard, the capsule forces the distal region to stretch and expand in diameter upon forced insertion within the distal region. Thus, the delivery device has a relatively low profile appropriate for traversing a patient's vasculature, such as across the aortic arch, in the delivery state. Conversely, in the deployed state, the capsule is readily received within the distal region, thereby permitting the stability tube to extend along, and thus support, a substantial length of the delivery sheath. In some embodiments, at least the distal region of the stability tube is a two or three layer extruded tube, with an inner layer exhibiting a highly stretchable or expandable characteristic, and an outer layer having one or more scoring lines formed therein. With this construction, upon insertion of the capsule within the distal region, the inner layer stretches and the outer layer splits along the scoring line.

Yet other aspects of the present disclosure relate to a system for repairing a defective heart valve of a patient. The system includes a prosthetic heart valve and the delivery device as described above. The prosthetic heart valve includes a stent frame and a valve structure attached to the frame and forming at least two valve leaflets. The prosthetic heart valve is radially self-expandable from a compressed arrangement to a normal, expanded arrangement. Upon assembly of the system to a delivery condition, the capsule compressively contains the prosthetic heart valve in the compressed arrangement over the inner shaft assembly. The system can be transitioned to a deployed condition in which the capsule is retracted from the prosthetic heart valve to permit the prosthesis to self-deploy toward the normal arrangement and release from the delivery device. In this regard, and as described above, the distal region radially expands upon slidable insertion of the capsule therein when transitioning to the deployed condition.

Yet other aspects in accordance with the present disclosure relate to a method of repairing a defective heart valve of a patient. The method includes receiving a delivery device loaded with a radially self-expandable prosthetic heart valve having a stent frame to which a valve structure is attached. The delivery device includes a delivery sheath having a capsule extending distally from a shaft and containing the prosthetic heart valve in a compressed arrangement in a delivery state of the delivery device. The delivery device further includes an outer stability tube coaxially received over the delivery sheath and including a distal region terminating at a distal end located proximal the capsule. The prosthetic heart valve is delivered, in the compressed arrangement, through a bodily lumen of the patient to an implantation site of the defective valve via the delivery device. In this regard, the delivery device has a low profile in the delivery state, with the outer diameter of the distal region being not greater than an outer diameter of the capsule. The capsule is proximally retracted from over the prosthetic heart valve and at least partially into the distal region of the stability tube, allowing the prosthetic heart valve to self-deploy from the delivery device and implant within the defective valve. Retraction of the capsule into the distal region causes the distal region to expand in diameter. In some embodiments, delivery of the prosthetic heart valve to the implantation site includes establishing an access portal to the bodily lumen of the patient with an introducer device including an introducer sheath and a valve. The prosthetic heart valve is inserted into the bodily lumen through the introducer valve, with hemostasis being established between the introducer valve and the stability tube.

BRIEF DESCRIPTION OF THE DRAWINGS

FIG. 6A is a side view of the distal region of FIG. 5A and in a second shape;

FIG. 6B is an end view of the stability tube of FIG. 6A;

FIG. 7A is a simplified side view of a portion of the system of FIG. 3 in a delivery condition including the delivery device of FIG. 4 loaded with the prosthetic heart valve of FIG. 2B and in a delivery state;

FIG. 7B is a simplified cross-sectional view of the system of FIG. 7A;

FIG. 8A is a simplified side view of the system of FIG. 7A in an intermediate stage of operation;

FIG. 8B is a simplified cross-sectional view of the system of FIG. 8A;

DETAILED DESCRIPTION

Figure 1A:
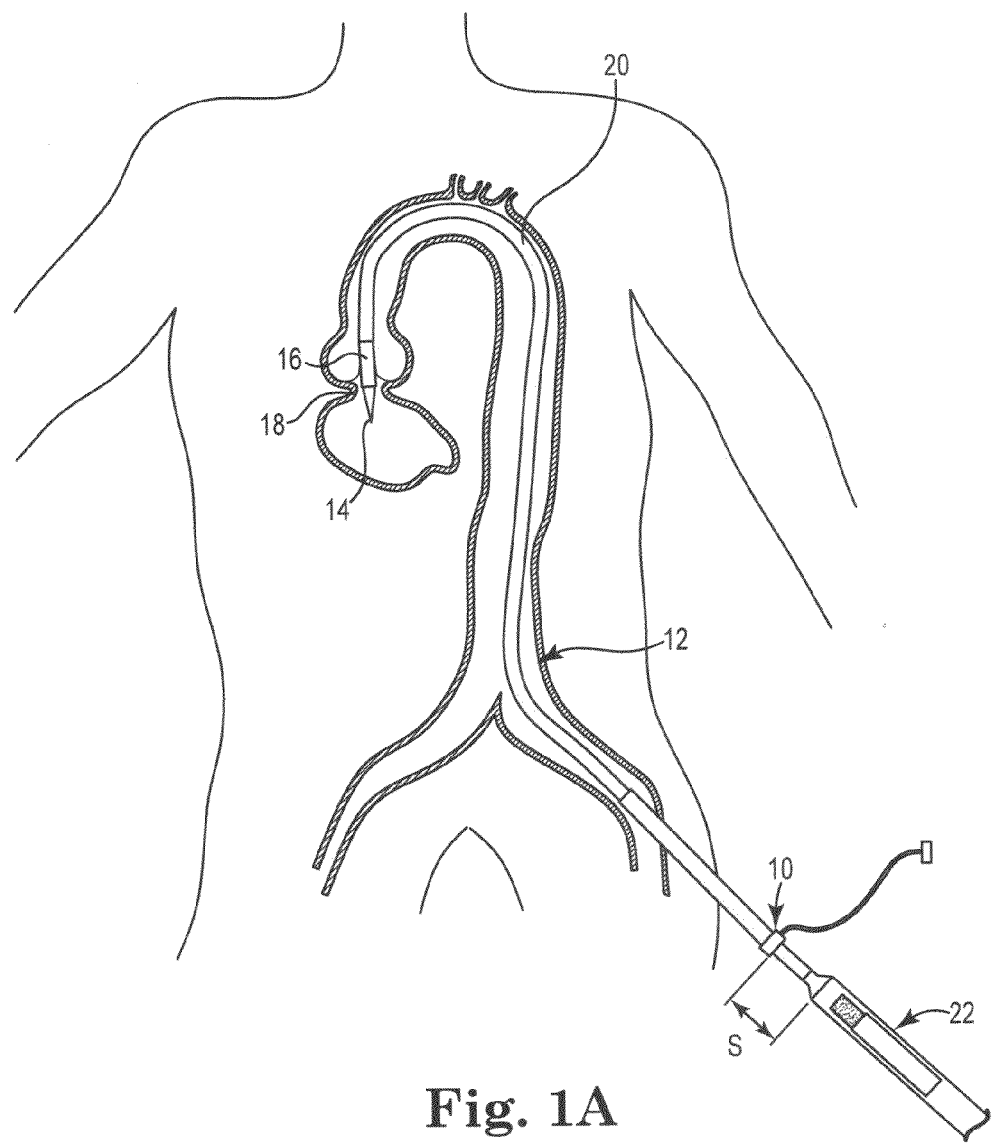
FIGS. 1A and 1B are simplified illustrations of conventional transcatheter delivery and implantation of a stented prosthetic heart valve.
Figure 1B:
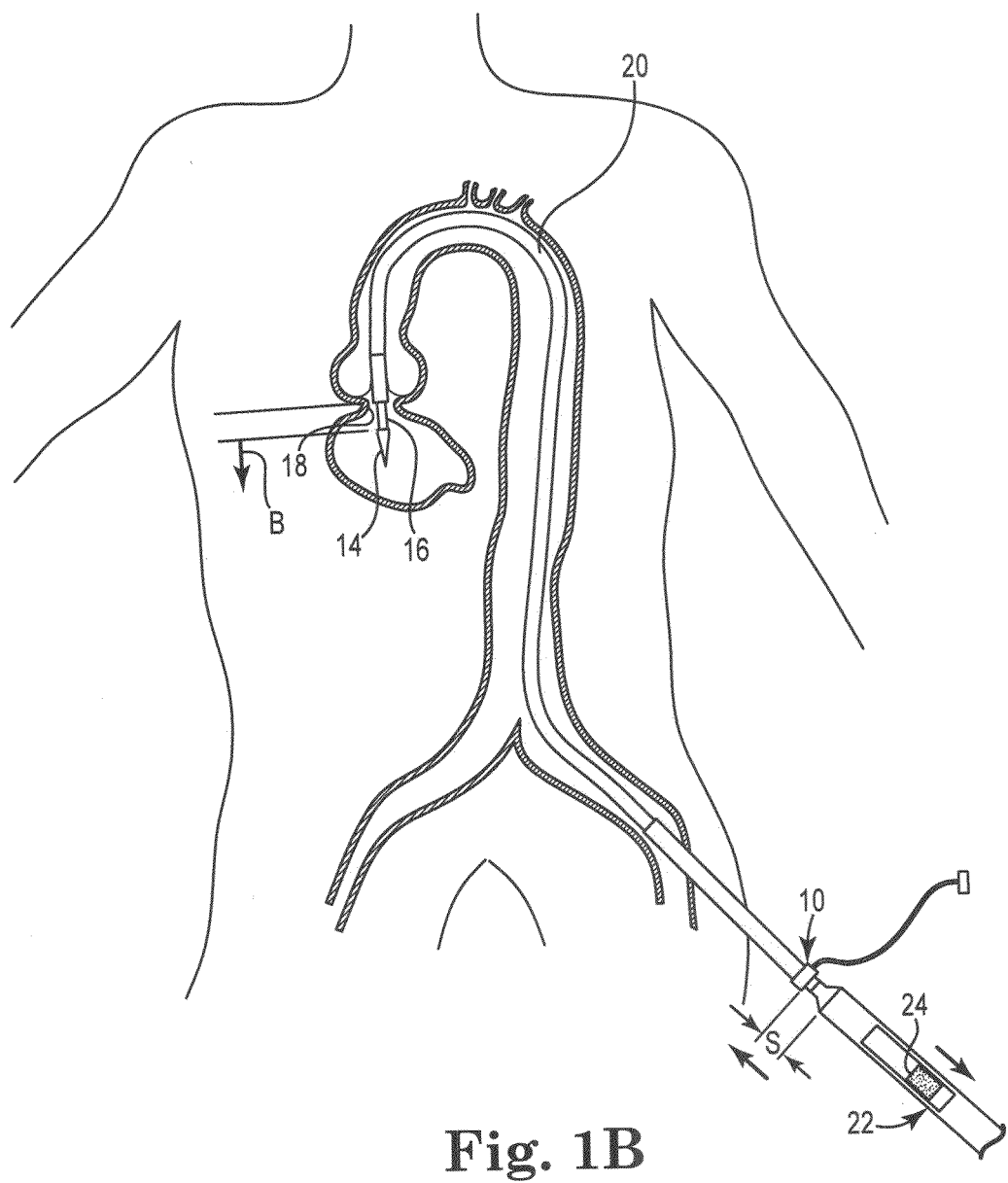

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valve leaflets can be mounted onto a delivery device. The stent frame support structures are configured so that they can be changed to their normal, expanded arrangement when desired, such as by the relative movement of one or more outer sheaths relative to a length of the stent frame.

The wires of these stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 2A:
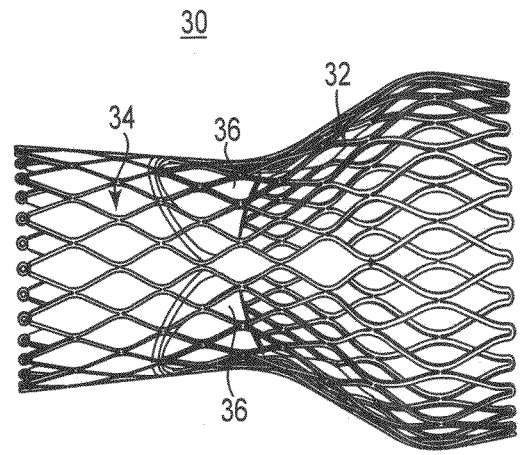
FIG. 2A is a side view of a stented prosthetic heart valve useful with systems, devices, and methods of the present disclosure and in a normal, expanded arrangement.
Figure 2B:
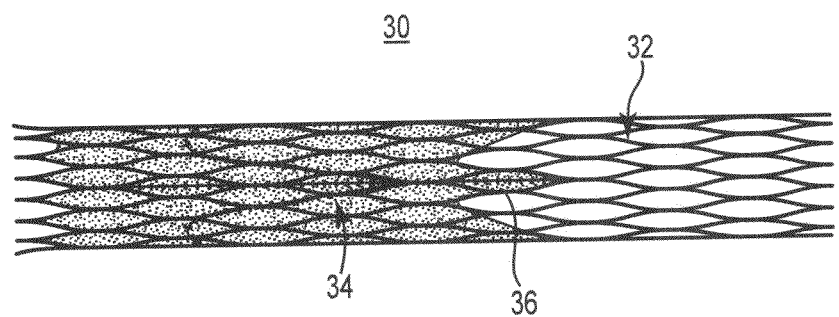
FIG. 2B is a side view of the prosthetic heart valve of FIG. 2A in a compressed arrangement.

With the above understanding in mind, one non-limiting example of a stented prosthetic heart valve 30 useful with systems and methods of the present disclosure is illustrated in FIG. 2A. As a point of reference, the prosthetic heart valve 30 is shown in a normal or expanded arrangement in the view of FIG. 2A; FIG. 2B illustrates the prosthetic heart valve 30 in a compressed arrangement (e.g., when compressively retained within an outer catheter or sheath). The prosthetic heart valve 30 includes a stent or stent frame 32 and a valve structure 34. The stent frame 32 can assume any of the forms described above, and is generally constructed so as to be self-expandable from the compressed arrangement (FIG. 2B) to the normal, expanded arrangement (FIG. 2A). In other embodiments, the stent frame 32 is expandable to the expanded arrangement by a separate device (e.g., a balloon internally located within the stent frame 32). The valve structure 34 is assembled to the stent frame 32 and provides two or more (typically three) leaflets 36. The valve structure 34 can assume any of the forms described above, and can be assembled to the stent frame 32 in various manners, such as by sewing the valve structure 34 to one or more of the wire segments defined by the stent frame 32.

With the but one acceptable construction of FIGS. 2A and 2B, the prosthetic heart valve 30 is configured for repairing an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 2A and 2B, the valve structure 34 extends less than the entire length of the stent frame 32, but in other embodiments can extend along an entirety, or a near entirety, of a length of the stent frame 32. A wide variety of other constructions are also acceptable and within the scope of the present disclosure. For example, the stent frame 32 can have a more cylindrical shape in the normal, expanded arrangement.

Figure 3:
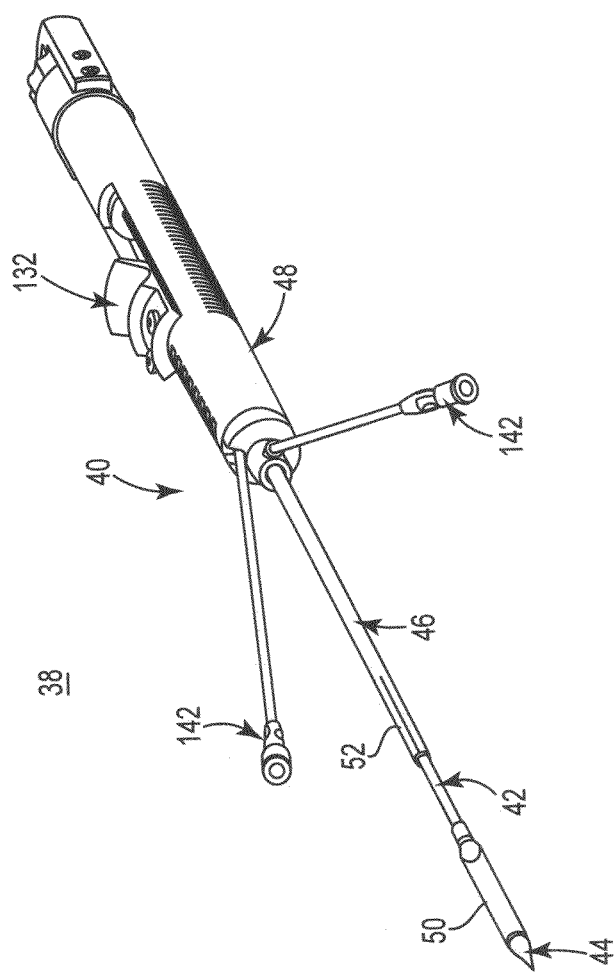
FIG. 3 is a perspective view of a stented prosthetic heart valve delivery system in accordance with principles of the present disclosure.

With the above understanding of the stented prosthetic heart valve 30 in mind, one embodiment of a system 38 for repairing a defective heart valve is shown in FIG. 3, and includes a delivery device 40 for percutaneously delivering and implanting the prosthetic heart valve 30. The delivery device 40 includes a delivery sheath assembly 42, an inner shaft assembly 44 (referenced generally), an outer stability tube 46, and a handle 48. Details on the various components are provided below. In general terms, however, the system 38 is transitionable from a loaded or delivery condition (shown in FIG. 3) in which the stented prosthetic heart valve (hidden in the view of FIG. 3) is contained within a capsule 50 of the delivery sheath assembly 42, to a deployed condition in which the capsule 50 is retracted from the prosthetic heart valve, thereby permitting the prosthetic heart valve to self-expand (or alternatively be caused to expand by a separate mechanism such as a balloon) and release from the delivery device 40. As part of this transitioning, the delivery sheath assembly 42 is slidable relative to the stability tube 46, with the stability tube 46 serving to frictionally isolate the delivery sheath assembly 42 from a separate introducer device (not shown). Further, a distal region 52 of the stability tube 46 has an expandable or stretchable attribute adapted to readily receive the capsule 50 when transitioning from a delivery state to a deployed state. With this construction, the stability tube 46 can be closely positioned to the capsule 50 during delivery and deployment, thereby desirably enhancing stabilization of the delivery sheath assembly 42.

Figure 4:
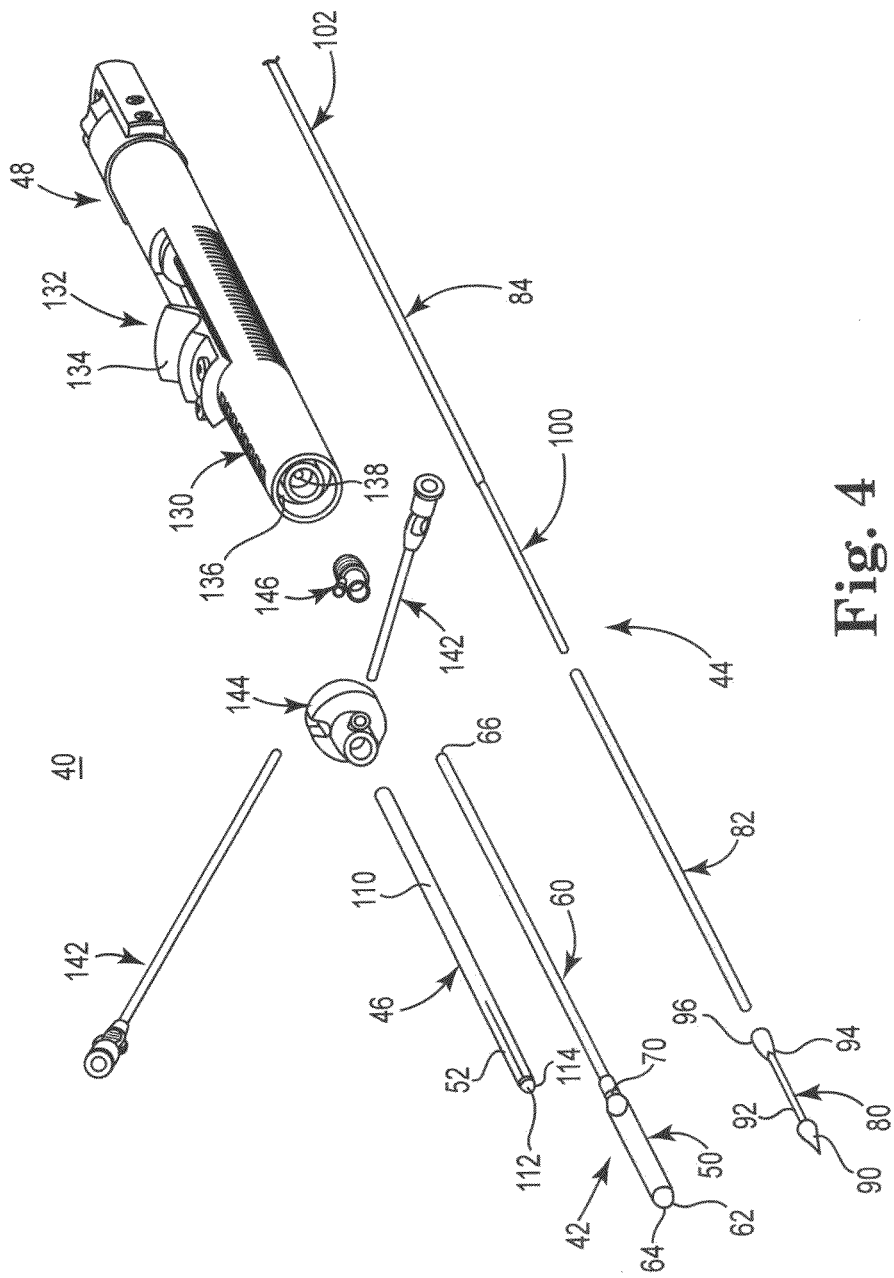
FIG. 4 is an exploded, perspective view of a delivery device portion of the system of FIG. 3.

Components in accordance with some embodiments of the delivery device 40 are shown in greater detail in FIG. 4. As a point of reference, various features of the components 42-48 reflected in FIG. 4 and described below can be modified or replaced with differing structures and/or mechanisms. Thus, the present disclosure is in no way limited to the delivery sheath assembly 42, the inner shaft assembly 44, the handle 48, etc., shown and described below. More generally, then, delivery devices in accordance with principles of the present disclosure provide features capable of compressively retaining a self-deploying stented prosthetic heart valve (e.g., the capsule 50), along with one or more components (e.g., the stability tube 46) capable of isolating the delivery sheath from an introducer device and having features that facilitate close positioning to the capsule 50.

In some embodiments, the delivery sheath assembly 42 includes the capsule 50 and a shaft 60, and defines a lumen 62 (referenced generally) extending from a distal end 64 to a proximal end 66. In some constructions, the capsule 50 and the shaft 60 are comprised of differing materials and/or constructions, with the capsule 50 having a longitudinal length approximating (e.g., slightly greater than) a length of the prosthetic heart valve 30 (FIG. 2B) to be used with the device 40. The capsule 50 is attached to, and extends distally from, the shaft 60 and in some embodiments has a more stiffened construction (as compared to a stiffness of the shaft 60) that exhibits sufficient radial or circumferential rigidity to overtly resist the expected expansive forces of the stented prosthetic heart valve 30 when compressed within the capsule 50. For example, the shaft 60 can be a polymer tube embedded with a metal braiding, whereas the capsule 50 includes a laser-cut metal tube that is optionally embedded within a polymer covering. Alternatively, the capsule 50 and the shaft 60 can have a more uniform construction (e.g., a continuous polymer tube). Regardless, the capsule 50 is constructed to compressively retain the stented prosthetic heart valve 30 at a predetermined diameter when loaded within the capsule 50, and the shaft 60 serves to connect the capsule 50 with the handle 48. To better accommodate a size of the compressed prosthesis 30 while at the same time maintaining an overall low profile, an outer diameter of the capsule 50 can be greater than an outer diameter of the shaft 60 in some embodiments, with the resultant construction providing the capsule 50 with a discernable proximal end 70. The shaft 60 (as well as the capsule 50) is constructed to be sufficiently flexible for passage through a patient's vasculature, yet exhibits sufficient longitudinal rigidity to effectuate desired axial movement of the capsule 50. In other words, proximal retraction of the shaft 60 is directly transferred to the capsule 50 and causes a corresponding proximal retraction of the capsule 50. In other embodiments, the shaft 60 is further configured to transmit a rotational force or movement onto the capsule 50.

The inner shaft assembly 44 can have various constructions appropriate for supporting a stented prosthetic heart valve within the capsule 50. For example, the inner shaft assembly 44 can include a retention member 80, an intermediate tube 82, and a proximal tube 84. In general terms, the retention member 80 is akin to a plunger, and incorporates features for retaining the stented prosthetic heart valve 30 (FIG. 2B) within the capsule 50 as described below. The intermediate tube 82 connects the retention member 80 to the proximal tube 84, with the proximal tube 84, in turn, coupling the inner shaft assembly 44 with the handle 48. The components 80-84 can combine to define a continuous lumen 86 (referenced generally) sized to slidably receive an auxiliary component such as a guide wire (not shown).

The retention member 80 can include a tip 90, a support tube 92, and a hub 94. The tip 90 forms or defines a nose cone having a distally tapering outer surface adapted to promote atraumatic contact with bodily tissue. The tip 90 can be fixed or slidable relative to the support tube 92. The support tube 92 extends proximally from the tip 90 and is configured to internally support a compressed, stented prosthetic heart valve generally disposed thereover, and has a length and outer diameter corresponding with dimensional attributes of the prosthetic heart valve. The hub 94 is attached to the support tube 92 opposite the tip 90 (e.g., adhesive bond) and provides a coupling structure 96 (referenced generally) configured to selectively capture a corresponding feature of the prosthetic heart valve. The coupling structure 96 can assume various forms, and is generally located along an intermediate portion of the inner shaft assembly 44. In some embodiments, the coupling structure 96 includes one or more fingers sized to be slidably received within corresponding apertures formed by the prosthetic heart valve stent frame 32 (FIG. 2A). For example, the stent frame 32 can form wire loops at a proximal end thereof that are releasably received over respective ones of the fingers when compressed within the capsule 50. Other releasable coupling arrangements are also acceptable, such as the hub 94 forming one or more slots sized to slidably receive a corresponding component(s) of the prosthetic heart valve (e.g., a bar or leg segment of the stent frame). Further, the inner shaft assembly 44 can incorporate additional structures and/or mechanisms that assist in temporarily retaining the prosthetic heart valve (e.g., a tubular segment biased over the coupling structure 96), such as described in U.S. Provisional Application Ser. No. 61/237,373 entitled "Transcatheter Valve Delivery Systems and Methods" filed Aug. 27, 2009 and the entire teachings of which are incorporated herein by reference.

The intermediate tube 82 is formed of a flexible material (e.g., PEEK), and is sized to be slidably received within the delivery sheath assembly 42 and in particular the shaft 60. The proximal tube 84 can include a leading portion 100 and a trailing portion 102. The leading portion 100 serves as a transition between the intermediate and proximal tubes 82, 84, and thus can be a flexible tubing (e.g., PEEK) having a diameter slightly less than that of the intermediate tube 82. The trailing portion 102 has a more rigid construction, configured for robust assembly with the handle 48. For example, the trailing portion 102 can be a metal hypotube, although other constructions are also acceptable. In yet other embodiments, the intermediate and proximal tubes 82, 84 are integrally formed as a single, homogenous tube or solid shaft.

The stability tube 46 includes or defines the distal region 52 and a proximal region 110. The stability tube 46 forms a lumen 112 (referenced generally) sized to be slidably received over the delivery sheath assembly 42 as described below, with the stability tube 46 terminating at a distal end 114.

Figure 5A:
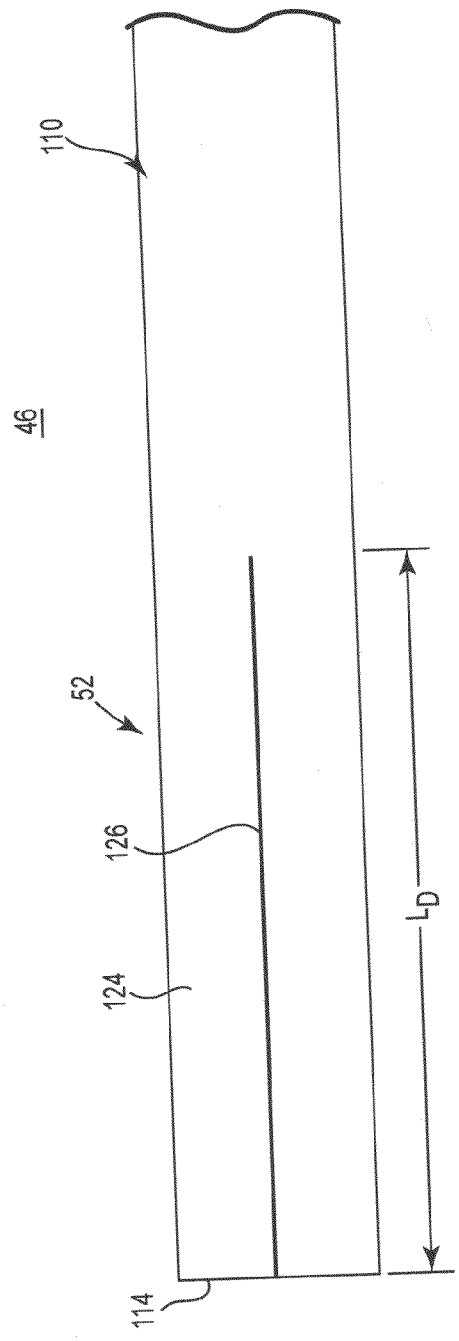
FIG. 5A is an enlarged side view of a distal region portion of a stability tube component of the delivery device of FIG. 4 in a first shape.
Figure 5B:
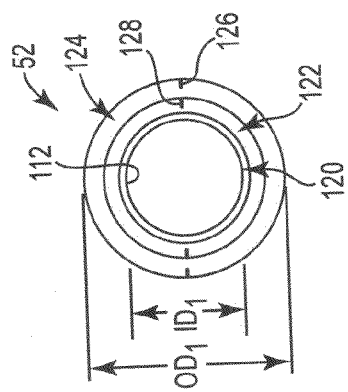
FIG. 5B is an end view of the distal region of FIG. 5A.

The distal region 52 is configured to be radially expandable or stretchable in response to an internally applied, radially expansive force from a first shape generally reflected in FIG. 4 to a second shape having an increased diameter. For example, FIGS. 5A and 5B illustrate the distal region 52 in the first shape. As shown, the distal region 52 is a generally tubular body formed by two or more layers. With the one acceptable construction of FIGS. 5A and 5B, for example, the distal region 52 includes an inner layer 120, an intermediate layer 122, and an outer layer 124 (as a point of reference, a thickness of the layers 120-124 is exaggerated in FIG. 5B for ease of explanation). One or more longitudinal scoring lines 126 (e.g., cuts, slits, perforations, etc.) are formed through a partial thickness of the outer layer 124. Optionally, one or more corresponding longitudinal scoring lines 128 can be formed through a partial thickness of the intermediate layer 122. The number and extent (e.g., radial depth) of the scoring lines 126, 128 is a function of the desired circumferential rigidity of the distal region as described below. The inner layer 120 is continuous or otherwise free of scoring lines or similar cuts. Other structures can be incorporated into the distal region 52, for example additional layers. Conversely, the intermediate layer 122 can be omitted. Regardless, in the first shape, the inner layer 120 defines an inner diameter $ID_1$ of the distal region 52, with a combined thickness of the layers 120-124 defining an outer diameter $OD_1$. The inner diameter $ID_1$ and the outer diameter $OD_1$ can be uniform along an entirety of the distal region 52, or alternatively can be characterized as nominal, maximum inner and maximum outer dimensions of the distal region 52. As a point of reference, a length $L_D$ of the distal region 52 can be defined as a longitudinal distance between the distal end 114 and a proximalmost end of the scoring lines 126, 128. For reasons made clear below, the distal region length $L_D$ approximates, or is slightly greater than, a longitudinal length of the capsule 50 (FIG. 4).

The layers 120-124 can be formed from various materials, such as polymer materials (e.g., polymer films). In general terms, however, a construction of the layers 120-124 is such that the inner layer 120 exhibits enhanced circumferential stretch properties as compared to those of the intermediate and outer layers 122, 124. Stated otherwise, the inner layer 120 will readily circumferentially stretch (e.g., plastically or elastically deform), whereas the intermediate and outer layers 122, 124 exhibit enhanced circumferential rigidity as compared to the inner layer 120. For example, in some constructions, the inner layer 120 is a stretchable polymer film such as high density polyethylene. The intermediate layer 122 can be a more structurally robust polymer film such as a linear low density polyethylene polymer available under the trade name Plexar® from Equistar Chemicals. The outer layer 124 is also a structurally robust polymer, such as a thermoplastic polyamide-based material available under the trade name Grilamide® from EMS-Grivory. A wide variety of other polymer materials are also envisioned. The materials selected for the layers 120-124 are amenable to trilayer extrusion in some embodiments, with the inner layer 120 being stretchable and the intermediate and outer layers 122, 124 providing enhanced circumferential rigidity.

By forming the score lines 126, 128 as longitudinally elongated, partial thickness cuts, slits, perforations, etc., a column strength of the distal region 52 is essentially the same as a column strength of the distal region 52 were the scoring lines 126, 128 not formed (e.g., where the stability tube 46 is formed as a continuous, homogenous tube, the column strength of the distal and proximal regions 52, 110 is substantially the same). However, the scoring lines 126, 128 in combination with the stretchable nature of the inner layer 120 permit the distal region 52 to readily expand to the second shape reflected, for example, in FIGS. 6A and 6B. In particular, when the distal region 52 is subjected to an internally expansive force, the inner layer 120 will stretch, radially expanding in diameter. The outer layer 124 internally separates or splits along the scoring lines 126, resulting in at least first and second outer layer segments 130a, 130b that are longitudinally separated from one another (along the distal region 52). Where three or more of the scoring lines 126 are formed, additional, longitudinally separated outer layer segments are defined in the second shape. With embodiments in which the intermediate layer 122 includes the scoring lines 128, internal separation or splitting also occurs, resulting in two (or more) longitudinally separated intermediate layer segments 132a, 132b. Alternatively, the intermediate layer 122 can be configured to exhibit enhanced stretching properties (e.g., akin to those of the inner layer 120); under these circumstances, the scoring lines 128 are omitted and the intermediate layer 122 instead stretches (instead of internally separating) in a manner akin to the inner layer 120 in response to the radially expansive force. Regardless, the distal region 52 experiences a collective increase in inner and outer diameter. In the second shape of FIGS. 6A and 6B, then, the distal region 52 has an inner diameter $ID_2$ and an outer diameter $OD_2$ that are greater than the corresponding diameters $ID_1$, $OD_1$ (FIGS. 5A and 5B) of the first shape.

The distal region 52 is constructed to readily transition from the first shape (FIG. 5B) to the second shape (FIG. 6B) in response to expected radially expansive forces generated by insertion of the capsule 50 (FIG. 4) within the lumen 112. To this end, and for reasons made clear below, the inner diameter $ID_1$ (FIG. 5B) in the first shape is less than a normal outer diameter of the capsule 50. So long as a circumferential rigidity of the capsule 50 is greater than a circumferential rigidity of the distal region 52, the capsule 50 will exert a radially expansive force onto the distal region 52 when inserted into the lumen 112. Thus, a thickness of at least the inner layer 120, materials of the layers 120-124 and the extent or depth of the scoring lines 126, 128 are selected as a function of the circumferential stiffness of the capsule 50. More particularly, the inner layer 120 thickness, material selections, and depth of the scoring lines 126, 128 combine to define an overall circumferentially rigidity for the distal region 52, with this so-defined circumferential rigidity being less or lower than the circumferential rigidity of the capsule 50. Were the distal region 52 (in the first shape) circumferentially more rigid than the capsule 50, the distal region 52 would not expand in response to attempted insertion of the capsule 50, effectively (and undesirably) preventing capsule insertion. With this in mind, then, the thickness and material of the inner layer 120 are a function of the capsule circumferential rigidity, appropriate to facilitate stretching of the inner layer 120 in response to insertion of the capsule 50. The thickness and/or materials of the intermediate and outer layers 122, 124 need not necessarily stretch. However, the depth and/or number of the scoring lines 126, 128 should be sufficient to "break" or fully split the corresponding layer 122, 124 upon insertion of the capsule 50. Thus, for example, where the outer layer 124 is otherwise circumferentially rigid (due to selected materials and/or thickness), the scoring lines 126 will have a more significant depth as compared to a less circumferentially rigid construction of the outer layer 124. More generally, then, construction of the distal region 52 entails initially evaluating the circumferential rigidity of the capsule 50, and then configuring the inner layer 120 to stretch and the outer layer 124 (as well as the intermediate layer 122 where provided) to separate or split (via the scoring lines 126, 128) in response to insertion of the so-constructed capsule 50.

Returning to FIG. 4, in some embodiments, except for the scoring lines 126, 128 (FIG. 5A), the proximal region 110 can have a construction identical to that of the distal region 52 (i.e., the stability tube 46 is a continuous, homogenous tube comprised of the trilayer extrusion described above). Alternatively, the regions 52, 110 can be differently constructed and subsequently assembled to one another. In yet other embodiments, one or more intermediate regions of varying construction are interposed between the distal and proximal regions 52, 110.

The proximal region 110 connects the distal region 52 with the handle 48. With this construction, the stability tube 46 serves as a stability shaft for the delivery sheath assembly 42, and has a length selected to extend over a significant (e.g., at least a majority), and in some embodiments at least 80%, of a length of the delivery sheath assembly 42 in distal extension from the handle 48. Further, the stability tube 46 exhibits sufficient radial flexibility to accommodate passage through a patient's vasculature (e.g., the femoral artery and the aortic arch).

The handle 48 generally includes a housing 130 and one or more actuator mechanism 132 (referenced generally). The housing 130 maintains the actuator mechanism 132, with the handle 48 configured to facilitate sliding movement of the delivery sheath assembly 42 relative to the inner shaft assembly 44 and the stability tube 46. The housing 130 can have any shape or size appropriate for convenient handling by a user. In one simplified construction of the actuator mechanism 132, a user interface or actuator 134 is slidably retained by the housing 130 and coupled to a connector body 136. The inner shaft assembly 44, and in particular the proximal tube 84 is slidably received within a passage 138 (referenced generally) of the connector body 136 and is rigidly coupled to the housing 130. With this but one acceptable construction, the deployment actuator 134 can be operated by a user to effectuate axial or longitudinal movement of the delivery sheath assembly 42 relative to the inner shaft assembly 44 and the stability tube 46. In some embodiments, the housing 130 can further incorporate a second actuator mechanism (not shown) that facilitates user-actuated movement of the stability tube 46 relative to the delivery sheath assembly 42. Further, the handle 48 can include other features, such as optional port assemblies 142, a cap 144, and/or a manifold 146 as shown.

FIGS. 7A and 7B illustrate, in simplified form, a distal portion of the system 38 in the delivery condition, including the stented prosthetic heart valve 30 loaded within the delivery device 40 such that the delivery device 40 is in the delivery state. In the loaded or delivery condition of the system 38, the prosthetic heart valve 30 is crimped over the inner shaft assembly 44 to engage the coupling structure 96. The capsule 50 compressively contains the prosthetic heart valve 30 in the compressed arrangement. As shown, with the delivery device 40 construction of FIGS. 7A and 7B, an outer diameter $OD_C$ of the capsule 50 can be greater than an outer diameter $OD_S$ of the shaft 60 as may be necessary for optimally retaining the prosthetic heart valve 30 in the compressed arrangement. Finally, the stability tube 46 is coaxially arranged over the shaft 60 of the delivery sheath assembly 42, with the distal end 114 located proximal the proximal end 70 of the capsule 50. For example, the distal end 114 can be immediately proximal the proximal end 70. Regardless, the distal region 52 assumes the first shape in the delivery state, with the distal region inner diameter $ID_1$ (FIG. 5B) approximating (e.g., within 5%) the outer diameter $OD_S$ of the shaft 60. The inner diameter of the proximal region 110 also approximates the shaft outer diameter $OD_S$, it being understood that a slight clearance (on the order of 1 French in some embodiments) can be provided. Thus, in the delivery state, the inner diameter $ID_1$ of the distal region 52 is less than the capsule outer diameter $OD_C$. In some embodiments, the distal region outer diameter $OD_1$ (FIG. 5B) in the delivery state is not greater than the capsule diameter $OD_C$, thereby providing an overall low profile attribute to the loaded delivery device 40. For example, the capsule 50 and the distal region 52 (in the first shape described above) can both have an outer diameter on the order of 16 French, although dimensions are also acceptable.

Transitioning of the delivery device 40 from the delivery state of FIGS. 7A and 7B to the deployment state generally entails proximal retraction of the capsule 50 from over the prosthetic heart valve 30. FIGS. 8A and 8B illustrate initial proximal movement of the delivery sheath assembly 42 (and in particular the capsule 50) in transitioning toward the deployment state, with the capsule 50 being partially retracted from the prosthetic heart valve 30. As the capsule 50 is proximally retracted, the proximal end 70 slides proximally beyond the distal end 114 of the stability tube 46, such that a portion 150 of the capsule 50 is within the distal region 52. As described above, the circumferential rigidity of the capsule 50 is greater than a collective circumferential rigidity of the distal region 52. As a result, the portion 150 of the capsule 50 otherwise within the distal region 52 exerts a radially expansive force onto the distal region 52. With additional reference to FIG. 5B, this force, in turn, causes the inner layer 120 to circumferentially stretch and radially expand. Further, the outer layer 124 is caused to split along the scoring lines 126. The intermediate layer 122 (where provided) similarly splits along the scoring lines 128 (or stretches when the scoring lines 128 are omitted). Effectively, then, because the collective circumferential rigidity of the distal region 52 is less than the circumferential rigidity of the capsule 50, as the capsule 50 is retracted within the distal region 52, the distal region 52 expands to accommodate the capsule 50.

Figure 9A:
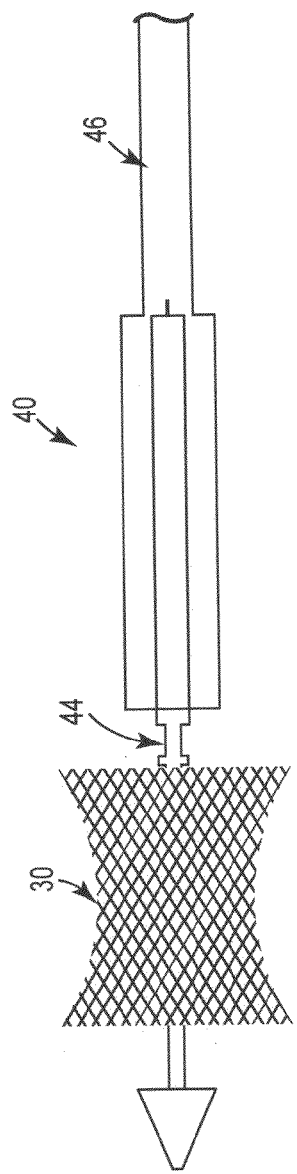
FIG. 9A is a simplified side view of the system of FIG. 7A and including the delivery device in a deployment state.
Figure 9B:
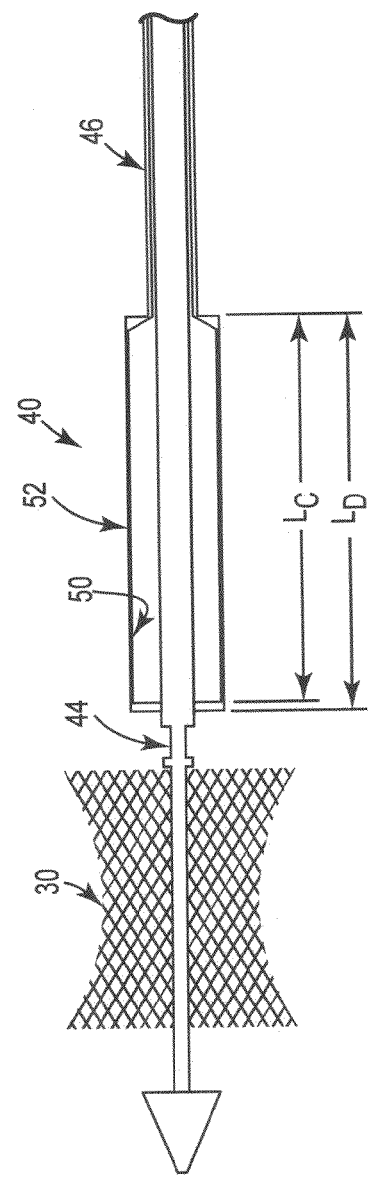
FIG. 9B is a simplified cross-sectional view of the system of FIG. 9A.

The fully deployed state of the delivery device 40 is reflected in FIGS. 9A and 9B. The capsule 50 is proximally retracted from the prosthetic heart valve 30, thereby allowing the prosthetic heart valve 30 to self-deploy from the inner shaft assembly 44. Further, the capsule 50 is entirely (or nearly entirely) within the distal region 52, with the distal region 52 having expanded in diameter to accommodate the capsule 50. As a point of reference, FIG. 9A reflects a comparison of the distal region length $L_D$ with a length $L_C$ of the capsule 50. As shown, the distal region length $L_D$ can be slightly greater than the capsule length $L_C$ such that an entirety of the capsule 50 can be disposed within the distal region 52.

Figure 10:
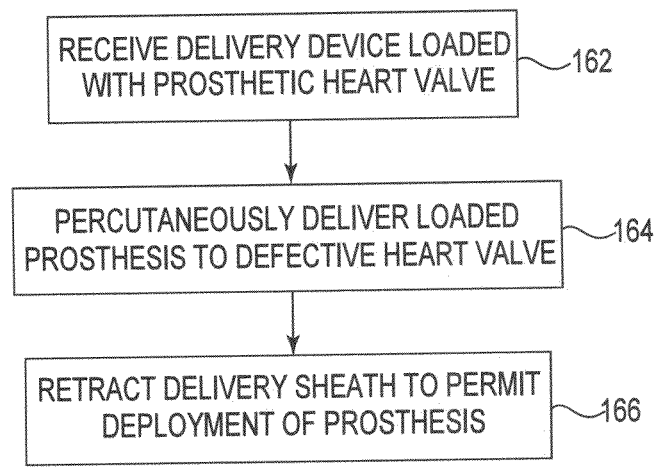
FIG. 10 is a flow diagram of a method for repairing a defective heart valve in accordance with principles of the present disclosure.

With reference to the delivery state (FIGS. 7A and 7B) and the flow diagram of FIG. 10, one method 160 for repairing a defective heart valve begins at 162 in which a clinician receives this system 38 in the loaded or delivery condition, including the delivery device 40 arranged in the delivery state. In particular, the stability tube 46 is arranged over the delivery sheath assembly shaft 60, with the distal region 52 assuming the first or low profile shape of FIGS. 7A and 7B. The delivery device 40 is then, at 164, manipulated to percutaneously deliver the prosthetic heart valve 30 (in the compressed arrangement) to a defective heart valve implantation site. For example, and with additional reference to FIG. 11A, the delivery device 40 can be used in conjunction with an introducer device 200. Introducer devices 200 are known in the art, and generally include an introducer sheath 202 and a valve 204. The introducer 202 is typically a resilient body. To access a bodily lumen (e.g., femoral artery) of the patient, an incision 206 is formed on the patient's skin, and the introducer sheath 202 inserted through the incision 206 and into the desired bodily lumen. The valve 204 fluidly closes the connection with the bodily lumen external the patient. The delivery device 40 is then inserted into the bodily lumen via the introducer device 200. As generally reflected in FIG. 11A, for example, the introducer sheath 202 has an inner diameter greater than an outer diameter of the stability tube 46 (as well as of the capsule 50), such that the capsule 50 can readily be delivered through the bodily lumen, directed to other branches of the patient's vasculature, and then to the defective heart valve implantation site 210 (e.g., aortic heart valve). In this regard, the introducer valve 204 frictionally contacts the stability tube 46, thereby establishing a low friction hemostasis seal around the stability tube 46. Notably, however, the stability tube 46 isolates the delivery sheath assembly 42 (and in particular the shaft 60) from the introducer sheath 202 and the valve 204. Stated otherwise, while the stability tube 46 is in physical contact with portions of the introducer device 200, the delivery sheath assembly 42 does not directly contact the introducer device 200.

Figure 11A:
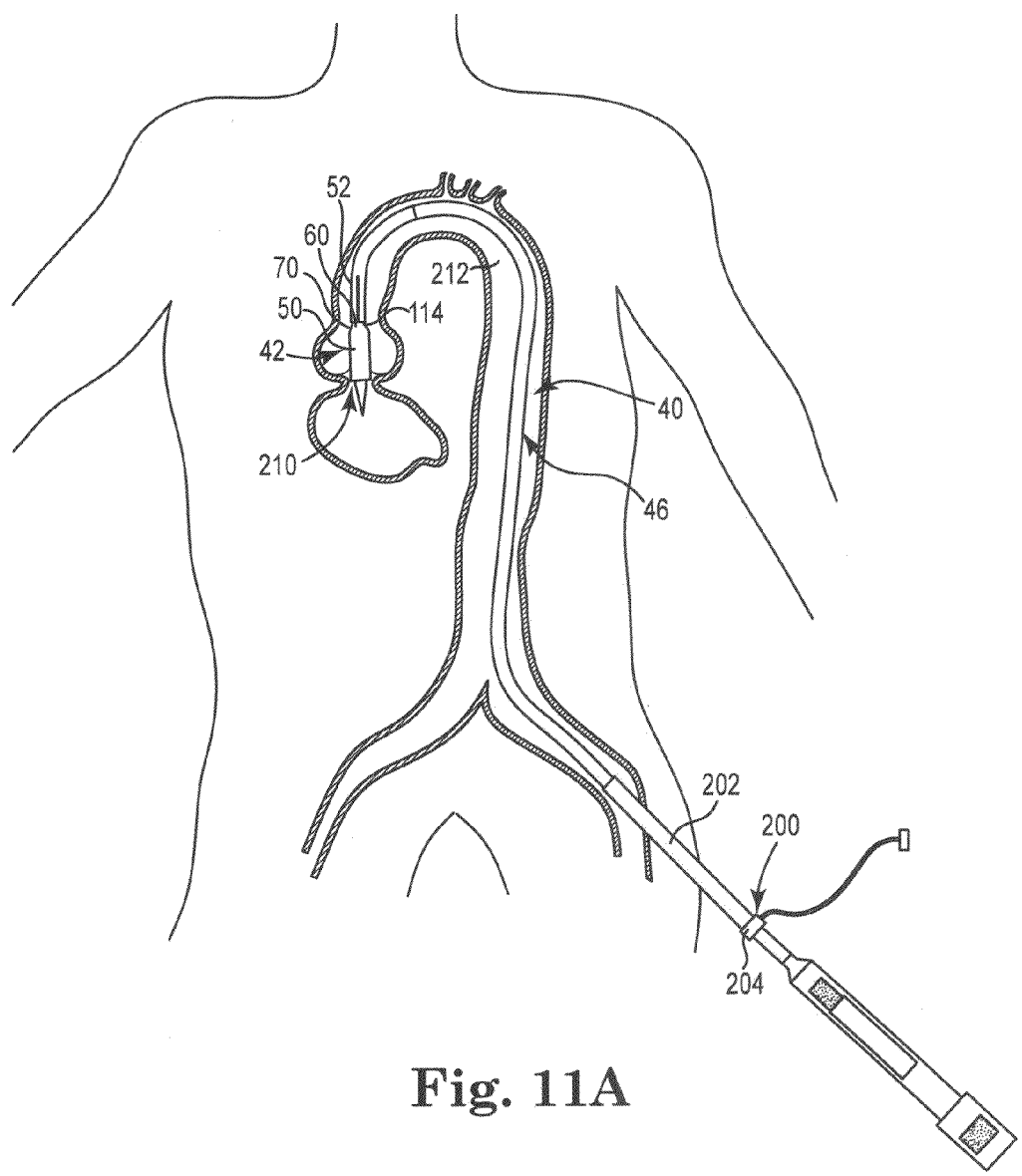
FIGS. 11A and 11B illustrate various steps of the method of FIG. 10.

As further reflected in FIG. 11A, as part of the initial delivery step, the delivery device 40 has an overall low profile due to the distal region 52 of the stability tube 46 assuming the first shape. By optionally locating the distal end 114 of the stability tube 46 in close proximity to the proximal end 70 of the capsule 50 (e.g., within a length that is less than the length of the capsule 50, or within 1 inch, or within 0.5 inch), the stability tube 46 overtly supports the delivery sheath assembly shaft 60 in traversing the tortuous vasculature, minimizing occurrences of kinks forming in the shaft 60 when, for example, moving across the aortic arch 212.

Figure 11B:
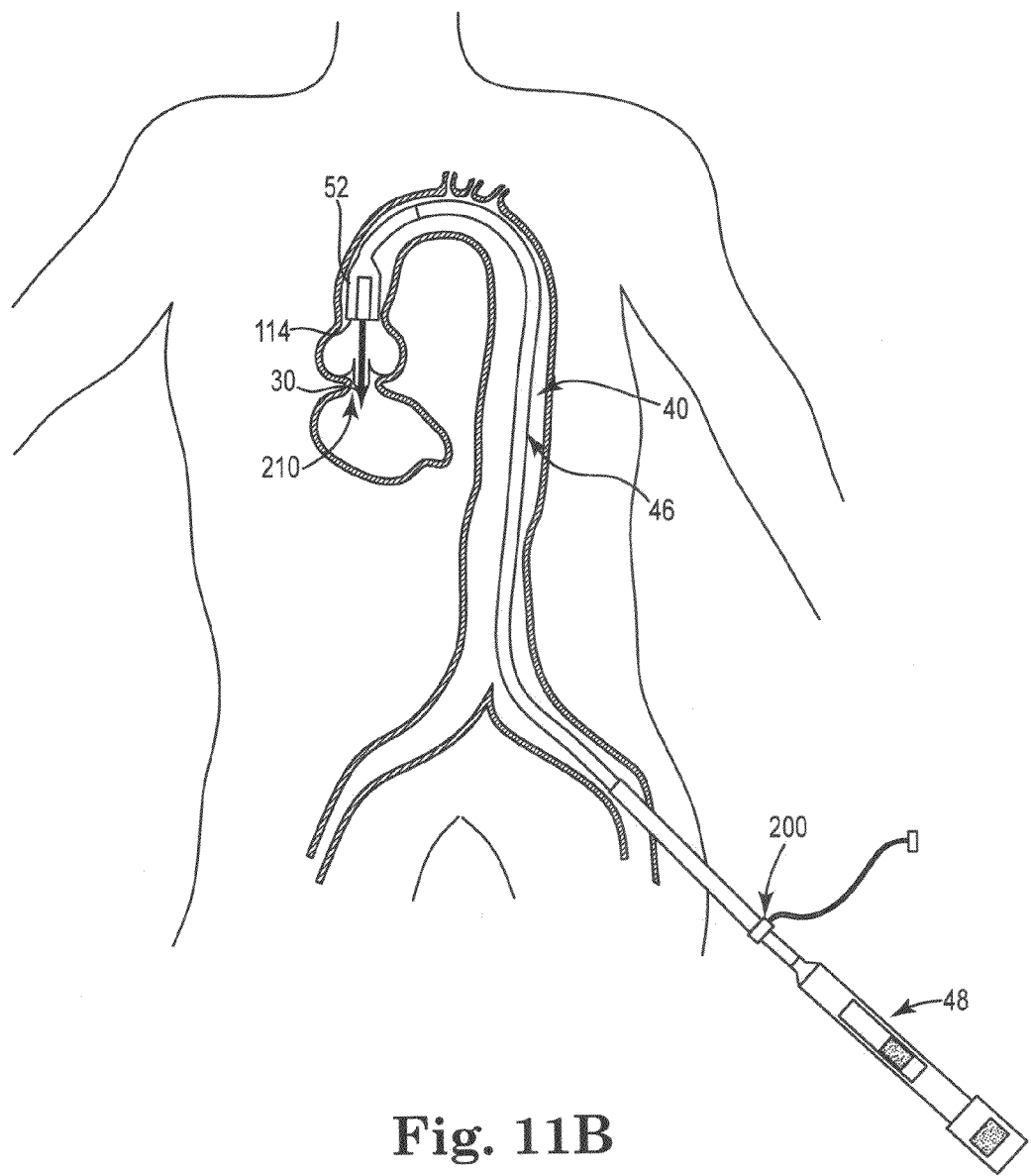

With reference to FIGS. 10 and 11B, at 166, the handle 48 is operated to distally retract the delivery sheath 42 (FIG. 4). In particular, the capsule 50 (hidden in FIG. 11B) is withdrawn from over the prosthetic heart valve 30 (drawn schematically in FIG. 11B), thereby permitting the prosthetic heart valve 30 to self-deploy from the delivery device 40. In this regard, due to the presence of the stability tube 46, with transitioning of the delivery device 40 from the delivery state to the deployment state via sliding of the delivery sheath assembly 42 (hidden in FIG. 11B), the delivery sheath assembly 42 does not bear against or otherwise frictionally interface with the introducer device 200. As a result, unlike previous percutaneous delivery procedures, the clinician and/or an assistant are not required to careful monitor a spacing between the handle 48 and the introducer device 200 while constantly correcting for any discrepancies as no frictional interface is established during retraction of the delivery sheath assembly 42. Further, because the distal end 114 of the stability tube 46 is in highly close proximity to the capsule 50 (FIG. 11A), an overall stabilization of the delivery sheath assembly 42 during a retraction thereof is provided. Regardless, and as described above, the distal region 52 of the stability tube 46 stretches or expands in response to retraction of the capsule 50 such that the capsule 50 is readily slidably received within the stability tube 46.

The stented prosthetic heart valve delivery systems, devices, and methods of the present disclosure provide a marked improvement over previous designs. By isolating the delivery sheath assembly from the introducer device, potential complications associated with previous designs are overcome. Further, by incorporating an expandable or stretchable feature into the outer stability tube, low profile delivery followed by fully supported retraction of the delivery sheath is provided.

Although the present disclosure has been described with reference to preferred embodiments, workers skilled in the art will recognize that changes can be made in form and detail without departing from the spirit and scope of the present disclosure. For example, the delivery systems shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices would further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter prosthetic valve is delivered through a percutaneous opening in the patient via the delivery device. Once the stented prosthetic heart valve is properly positioned, the balloon catheter is operated to inflate the balloon, thus transitioning the stented prosthesis to an expanded arrangement.

What is claimed is:

1. A delivery device for percutaneously delivering a stented prosthetic heart valve, the prosthetic heart valve being radially self-expandable from a compressed arrangement to a normal, expanded arrangement, the delivery device comprising:
   an inner shaft assembly including a coupling structure configured to selectively engage prosthetic heart valve;
   a delivery sheath assembly slidably disposed over the inner shaft assembly and including a distal capsule and a proximal shaft, wherein the capsule is configured to compressively contain the prosthetic heart valve in a compressed arrangement;
   an outer stability tube coaxially received over the proximal shaft, the stability tube including a proximal region and a distal region;

wherein a circumferential rigidity of the capsule is greater than a circumferential rigidity of the distal region; and
a handle maintaining the inner shaft assembly, the delivery sheath assembly, and the stability tube, the handling including:
a housing,
an actuator mechanism maintained by the housing and coupled to the proximal shaft, wherein the actuator mechanism is operable to selectively move the delivery sheath assembly relative to the inner shaft assembly and the stability tube; wherein the delivery device is configured to provide:
a delivery state in which the capsule compressively contains the prosthetic heart valve and the distal region of the stability tube is proximal the capsule, an inner diameter of the distal region being less than an outer diameter of the capsule in the delivery state,
a deployed state in which the capsule is withdrawn from the prosthetic heart valve and at least partially into the distal region to permit the prosthetic heart valve to self-deploy, wherein the capsule forces the distal region to expand in diameter upon placement within the distal region.

2. The delivery device of claim 1, wherein the outer diameter of the capsule is greater than an outer diameter of the shaft.

3. The delivery device of claim 2, wherein the inner diameter of the distal region approximates the outer diameter of the shaft in the delivery state.

4. The delivery device of claim 3, wherein the outer diameter of the distal region approximates the outer diameter of the capsule in the delivery state.

5. The delivery device of claim 1, wherein the distal region includes a tubular body formed by at least a first layer and a second layer, and further wherein at least one scoring line is formed in the second layer such that upon sliding placement of the capsule within the distal region, the second layer splits along the scoring line and the first layer circumferentially stretches.

6. The delivery device of claim 5, wherein the second layer is external the first layer.

7. The delivery device of claim 5, wherein the first layer is formed from a polymer material differing from a polymer material of the second layer.

8. The delivery device of claim 7, wherein the polymer material of the first layer is high density polyethylene.

9. The delivery device of claim 5, wherein the first layer is characterized by the absence of a scoring line.

10. The delivery device of claim 5, wherein the scoring line extends through less than an entire thickness of the second layer.

11. The delivery device of claim 5, wherein the first and second layers are formed as a co-extruded tube.

12. The delivery device of claim 5, wherein a longitudinal length of the scoring line is greater than a longitudinal length of the capsule.

13. The delivery device of claim 5, wherein the tubular body further includes a third layer disposed over the second layer, the third layer defining at least one scoring line configured such that upon sliding placement of the capsule within the distal region, the third layer splits in tandem with the second layer.

14. The delivery device of claim 13, wherein the first layer is an inner layer, the second layer is an intermediate layer, and the third layer is an outer layer, and further wherein each of the layers is formed from a different polymer material.

15. The delivery device of claim 5, wherein the distal region and the proximal region are defined by a single, homogenous tube.

16. A system for repairing a defective heart valve of a patient, the system comprising:
a prosthetic heart valve including a stent frame and a valve structure attached to the frame and forming at least two valve leaflets, the prosthetic heart valve being radially self-expandable from a compressed arrangement to a normal, expanded arrangement; and
a delivery device comprising:
an inner shaft assembly including a coupling structure configured to selectively engage the prosthetic heart valve,
a delivery sheath assembly slidably disposed over the inner shaft assembly and including a distal capsule and a proximal shaft, wherein the capsule is configured to compressively contain the prosthetic heart valve in the compressed arrangement,
an outer stability tube coaxially received over the proximal shaft such that the proximal shaft is slidable relative to the stability tube, the stability tube including a proximal region and a distal region terminating at a distal end,
wherein a circumferential rigidity of the capsule is greater than a circumferential rigidity of the distal region,
a handle maintaining the inner shaft assembly, the delivery sheath assembly and the stability tube, the handle including:
a housing,
an actuator mechanism maintained by the housing and coupled to the proximal shaft, wherein the actuator mechanism is operable to selectively move the delivery sheath assembly relative to the inner shaft assembly and the stability tube; wherein the system is configured to provide:
a loaded condition in which the capsule compressively contains the prosthetic heart valve over the inner shaft assembly in the compressed arrangement, the distal end of the stability tube located immediately proximal the capsule, and the distal region defining an inner diameter that is less than an outer diameter of the capsule,
a deployed condition in which the capsule is retracted from the prosthetic heart valve to permit the prosthetic heart valve to self-deploy toward the normal arrangement and release from the delivery device,
wherein the system transitions from the loaded condition to the deployed condition by proximally sliding the delivery sheath assembly relative to the inner shaft assembly and the stability tube, including the capsule at least partially sliding within the distal region and forcing the distal region to expand in diameter.

17. The system of claim 16, wherein the outer diameter of the capsule is greater than an inner diameter of the shaft.

18. The system of claim 16, wherein a relationship of the circumferential rigidities of the capsule and the distal region is such that the capsule applies a radially expansive force to an interior of the distal region sufficient to cause the distal region to expand in diameter proximal the prosthetic heart valve.

19. The system of claim 16, wherein the distal region includes a tubular body formed by at least a first layer and a second layer, and further wherein at least one scoring line is formed in the second layer such that upon placement of the capsule within the distal region, the second layer splits along the scoring line and the first layer circumferentially stretches.

20. The system of claim 19, wherein the first layer is formed from a polymer material differing from a polymer material of the second layer.

21. The system of claim 19, wherein the first layer is characterized by the absence of a scoring line.

22. The system of claim 21, wherein the scoring line extends through less than an entire thickness of the second layer.

23. The system of claim 19, wherein a longitudinal length of the scoring line is greater than a longitudinal length of the capsule.

24. The system of claim 19, wherein the tubular body further includes a third layer disposed over the second layer, the third layer defining at least one scoring line configured such that upon sliding placement of the capsule within the distal region, the third layer splits in tandem with the second layer.

25. The system of claim 16, wherein in the loaded state, a longitudinal distance between the distal end of the stability tube and a proximal end of the capsule is less than a longitudinal length of the capsule.

\* \* \* \* \*